(12) United States Patent
Murasawa et al.

(10) Patent No.: US 10,687,841 B2
(45) Date of Patent: Jun. 23, 2020

(54) ULTRASONIC SURGICAL SYSTEM

(71) Applicant: OLYMPUS CORPORATION, Hachioji-shi, Tokyo (JP)

(72) Inventors: Keiko Murasawa, Tachikawa (JP); Yasuo Tanigami, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 264 days.

(21) Appl. No.: 15/908,230

(22) Filed: Feb. 28, 2018

(65) Prior Publication Data

US 2018/0185054 A1 Jul. 5, 2018

Related U.S. Application Data

(63) Continuation of application No. PCT/JP2016/075083, filed on Aug. 26, 2016.

(30) Foreign Application Priority Data

Aug. 28, 2015 (WO) .................. PCT/JP2015/074480
Mar. 31, 2016 (WO) .................. PCT/JP2016/060716

(51) Int. Cl.
*A61B 17/16* (2006.01)
*A61B 17/32* (2006.01)
(Continued)

(52) U.S. Cl.
CPC ...... *A61B 17/320068* (2013.01); *A61B 17/16* (2013.01); *A61B 17/29* (2013.01);
(Continued)

(58) Field of Classification Search
CPC . A61B 17/16; A61B 17/1622; A61B 17/1624; A61B 17/1628; A61B 17/1659;
(Continued)

(56) References Cited

U.S. PATENT DOCUMENTS 3,589,363 A 6/1971 Banko et al.
4,827,911 A * 5/1989 Broadwin ........ A61B 17/22012
310/17
(Continued)

FOREIGN PATENT DOCUMENTS

JP H08-187265 A 7/1996
JP H10-504732 A 5/1998
(Continued)

OTHER PUBLICATIONS

Aug. 8, 2019 Office Action issued in U.S. Appl. No. 14/867,970.
(Continued)

*Primary Examiner* — Eric S Gibson
(74) *Attorney, Agent, or Firm* — Oliff PLC

(57) ABSTRACT

An ultrasonic surgical includes an output unit, a transducer, a probe, an excision unit, and, a controller. The output unit generates a driving power. The transducer is connected to the output unit. The transducer converts the driving power into ultrasonic vibration. The probe transmits the ultrasonic vibration. The excision unit is provided in the probe. The excision unit is in contact with a predetermined portion of the cartilage. The excision unit heats the predetermined portion of the cartilage by ultrasonic vibration converted based on the driving power. The excision unit excises the cartilage by receiving pressure by an operator while being in contact with the cartilage. The controller controls the driving power output from the output unit so that the predetermined portion of the cartilage is heated to a temperature of 120° C. or higher within 2.2 seconds.

6 Claims, 15 Drawing Sheets

(51) Int. Cl.
*A61B 17/29* (2006.01)
*A61B 17/3205* (2006.01)
*A61B 17/00* (2006.01)

(52) U.S. Cl.
CPC .......... *A61B 17/32* (2013.01); *A61B 17/3205* (2013.01); *A61B 2017/00084* (2013.01); *A61B 2017/320069* (2017.08)

(58) Field of Classification Search
CPC . A61B 17/1662; A61B 17/1675; A61B 17/32; A61B 17/320068; A61B 2017/320069; A61B 2017/320072; A61B 2017/320074; A61B 2017/320075; A61B 2017/320077
See application file for complete search history.

(56) References Cited

U.S. PATENT DOCUMENTS

| | | | |
|---|---|---|---|
| 5,520,612 A | | 5/1996 | Winder et al. |
| 6,068,628 A * | | 5/2000 | Fanton ............ A61B 17/320016 606/28 |
| 6,379,371 B1 * | | 4/2002 | Novak ............ A61B 17/320068 606/169 |
| 6,443,969 B1 * | | 9/2002 | Novak ............ A61B 17/320068 606/169 |
| 6,544,260 B1 * | | 4/2003 | Markel ........... A61B 17/320016 606/41 |
| 6,671,535 B1 * | | 12/2003 | McNichols .......... A61B 5/0008 600/407 |
| 9,782,218 B2 * | | 10/2017 | Konishi ............ A61B 18/1445 |
| 9,788,852 B2 * | | 10/2017 | Voic ................ A61B 17/14 |
| 2003/0073987 A1 * | | 4/2003 | Sakurai ................ A61B 18/08 606/28 |
| 2006/0047331 A1 * | | 3/2006 | Lax ................... A61B 18/148 607/99 |
| 2006/0142775 A1 | | 6/2006 | Heneberry et al. |
| 2008/0009848 A1 * | | 1/2008 | Paraschiv ....... A61B 17/320068 606/34 |
| 2008/0058845 A1 * | | 3/2008 | Shimizu ................ A61B 17/29 606/169 |
| 2008/0234709 A1 | | 9/2008 | Houser |
| 2009/0024161 A1 * | | 1/2009 | Bonutti ............ A61B 17/0401 606/213 |
| 2012/0078278 A1 | | 3/2012 | Bales, Jr. et al. |
| 2014/0135663 A1 * | | 5/2014 | Funakubo ....... A61B 17/320068 601/2 |
| 2015/0005771 A1 * | | 1/2015 | Voic ................ A61B 17/14 606/79 |
| 2015/0005774 A1 * | | 1/2015 | Voic ............ A61B 17/320068 606/82 |
| 2015/0005775 A1 * | | 1/2015 | Voic ............ A61B 17/320068 606/83 |
| 2015/0088137 A1 * | | 3/2015 | Manna ................ A61B 17/142 606/79 |
| 2016/0249975 A1 * | | 9/2016 | Konishi ............ A61B 18/1445 606/45 |
| 2017/0086872 A1 * | | 3/2017 | Tanigami .......... A61B 17/3205 |
| 2017/0086874 A1 * | | 3/2017 | Tanigami ....... A61B 17/320068 |
| 2017/0086875 A1 * | | 3/2017 | Tanigami ....... A61B 17/320016 |
| 2017/0156737 A1 * | | 6/2017 | Tanigami ....... A61B 17/320068 |
| 2017/0165507 A1 * | | 6/2017 | Tanigami ................ A61N 7/02 |
| 2018/0185054 A1 * | | 7/2018 | Murasawa ............. A61B 17/16 |

FOREIGN PATENT DOCUMENTS

| | | |
|---|---|---|
| JP | 2000-217835 A | 8/2000 |
| JP | 2006-000322 A | 1/2006 |
| JP | 2006-187617 A | 7/2006 |
| JP | 2015-511860 A | 4/2015 |
| WO | 2015/093409 A1 | 6/2015 |
| WO | 2017/037790 A1 | 3/2017 |
| WO | 2017/038142 A1 | 3/2017 |
| WO | 2017/038722 A1 | 3/2017 |

OTHER PUBLICATIONS

Nov. 24, 2015 International Search Report issued in International Patent Application No. PCT/JP2015/074480.
Jun. 28, 2016 International Search Report issued in International Patent Application No. PCT/JP2016/060716.
Nov. 22, 2016 International Search Report issued in International Patent Application No. PCT/JP2016/075083.
Mar. 6, 2018 International Preliminary Report on Patentability issued in International Application No. PCT/JP2016/075083.
Mar. 6, 2018 International Preliminary Report on Patentability issued in International Application No. PCT/JP2015/074480.
Mar. 6, 2018 International Preliminary Report on Patentability issued in International Application No. PCT/JP2016/060716.
May 14, 2018 Office Action issued in U.S. Appl. No. 14/867,970.
Wiegand et al., "Comparative Calorimetric Analysis of 13 Different Types of Human Healthy and Pathologic Callogen Tissues," Thermochimica Acta, vol. 568, pp. 171-174, Jul. 8, 2013.
Oct. 5, 2017 Office Action Issued in U.S. Appl. No. 14/867,970.
Jun. 6, 2017 Office Action issued in Japanese Patent Application No. 2017-516985.
Mar. 7, 2018 U.S. Office Action Issued in U.S. Appl. No. 15/085,370.
Mar. 13, 2018 Office Action issued in U.S. Appl. No. 15/386,483.
U.S. Appl. No. 14/867,970, filed Sep. 28, 2015 in the name of Tanigami et al.
U.S. Appl. No. 15/085,370, filed Mar. 30, 2016 in the name of Tanigami et al.
U.S. Appl. No. 15/386,483, filed Dec. 21, 2016 in the name of Tanigami et al.
Jan. 29, 2019 Extended Search Report issued in European Patent Application No. 16841754.1.
Dec. 11, 2018 Office Action issued in U.S. Appl. No. 14/867,970.
Oct. 4, 2019 Office Action issued in Korean Application No. 10-2018-7006487.
Feb. 3, 2020 Office Action issued in Chinese Patent Application No. 201680050246.7.

* cited by examiner

F I G. 4

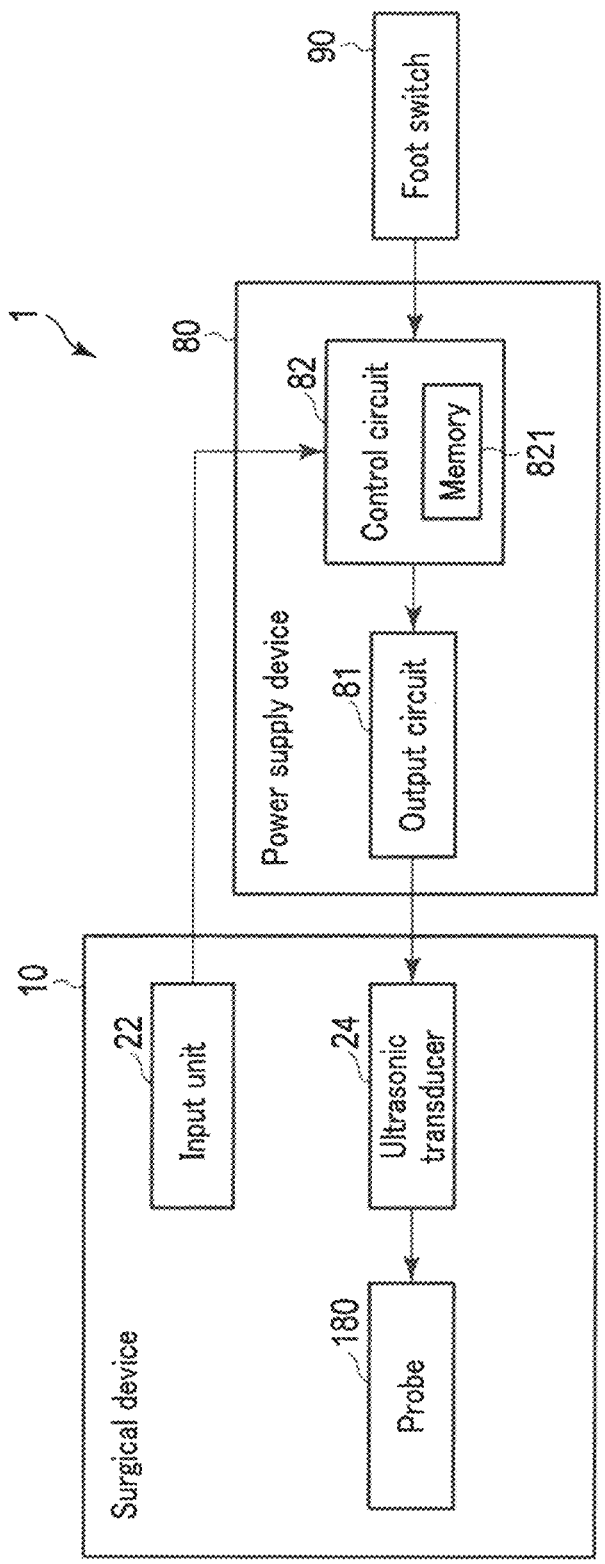
F I G. 8

| Cartilage | Device | Image of tissue (Representative example) | | Heat insult | Surface roughness |
|---|---|---|---|---|---|
| | | Low-magnification | High-magnification | | |
| | RF | 4X magnification | 40X magnification | Deep and widespread | Cells remarkably deformed by transpiration and deformation, bubbles dispersed, and uneven |
| | US | 4X magnification | 40X magnification | Only directly under excision edge | Mostly flat and smooth, cells directly under excision edge seem to be compressed |
| | BUR | 4X magnification | 40X magnification | Only directly under excision edge | Cells directly under excision edge become villus-like shaped, without retaining its original shape |

F I G. 11

ULTRASONIC SURGICAL SYSTEM

CROSS-REFERENCE TO RELATED APPLICATIONS

This application is a Continuation application of PCT Application No. PCT/JP2016/075083, filed Aug. 26, 2016 and based upon and claiming the benefit of priority from the prior PCT Applications No. PCT/JP2015/074480, filed Aug. 28, 2015 and No. PCT/JP2016/060716, filed Mar. 31, 2016, the entire contents of both of which are incorporated herein by reference.

BACKGROUND OF THE INVENTION

1. Field of Invention

The present invention relates to an ultrasonic surgical system.

2. Description of Related Art

Surgical devices capable of treating cartilage are suggested as an excision device for treating living tissue in Jpn. Pat. Appln. KOKAI Publication No. 2006-187617, for example. The surgical excision device suggested in Jpn. Pat. Appln. KOKAI Publication No. 2006-187617 includes a shaft and a distal end for tissue operation. A lumen is formed in the shaft. The distal end for tissue operation is formed at the distal end of the shaft and has a plurality of excision grooves and an opening through which the distal end communicates with the lumen of the shaft. The surgical excision device having the aforementioned structure rotates the shaft to bring the rotating distal end for tissue operation into contact with cartilage to excise the cartilage.

The surgical excision device suggested in Jpn. Pat. Appln. KOKAI Publication No. 2006-187617 rotates the distal end for tissue operation to catch the cartilage in the distal end, and excises the cartilage. In this process, it is easy for a surface of the cartilage after excision to become rough.

BRIEF SUMMARY OF THE INVENTION

According to an aspect of the invention, an ultrasonic surgical system for treating cartilage comprises: an output unit configured to generate a driving power; a transducer connected to the output unit, and configured to convert the driving power into ultrasonic vibration; a probe connected to the transducer, and configured to transmit the ultrasonic vibration; an excision unit provided in the probe, the excision unit being in contact with a predetermined portion of the cartilage, heating the predetermined portion of the cartilage by ultrasonic vibration converted based on the driving power, and excising the cartilage by receiving pressure by an operator while being in contact with the cartilage; and a controller configured to control the driving power output from the output unit so that the predetermined portion of the cartilage is heated to a temperature of 120° C. or higher within 2.2 seconds.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 4 illustrates a surface and a cross sectional view of cartilage for each of the temperatures when the soldering iron is pressed onto cartilage.

FIG. 8 is a block diagram showing a main configuration of the ultrasonic surgical system according to the first embodiment of the present invention.

FIG. 11 illustrates the comparison of cartilage excision results between a radio-frequency surgical system (RF), an ultrasonic surgical system (US), and a surgical system using a drill (BUR).

DETAILED DESCRIPTION OF THE INVENTION

Hereinafter, embodiments will be described with reference to the drawings.

First, the basic principle of the operation of the surgical system according to the present embodiment will be described. The surgical system according to the present embodiment is a surgical system for excising cartilage. Based on the applicant's analysis, excision of cartilage is performed in a mechanism different from the excision of different bone material such as cortical bone and cancellous bone. The details will be described below.

Figure 1:
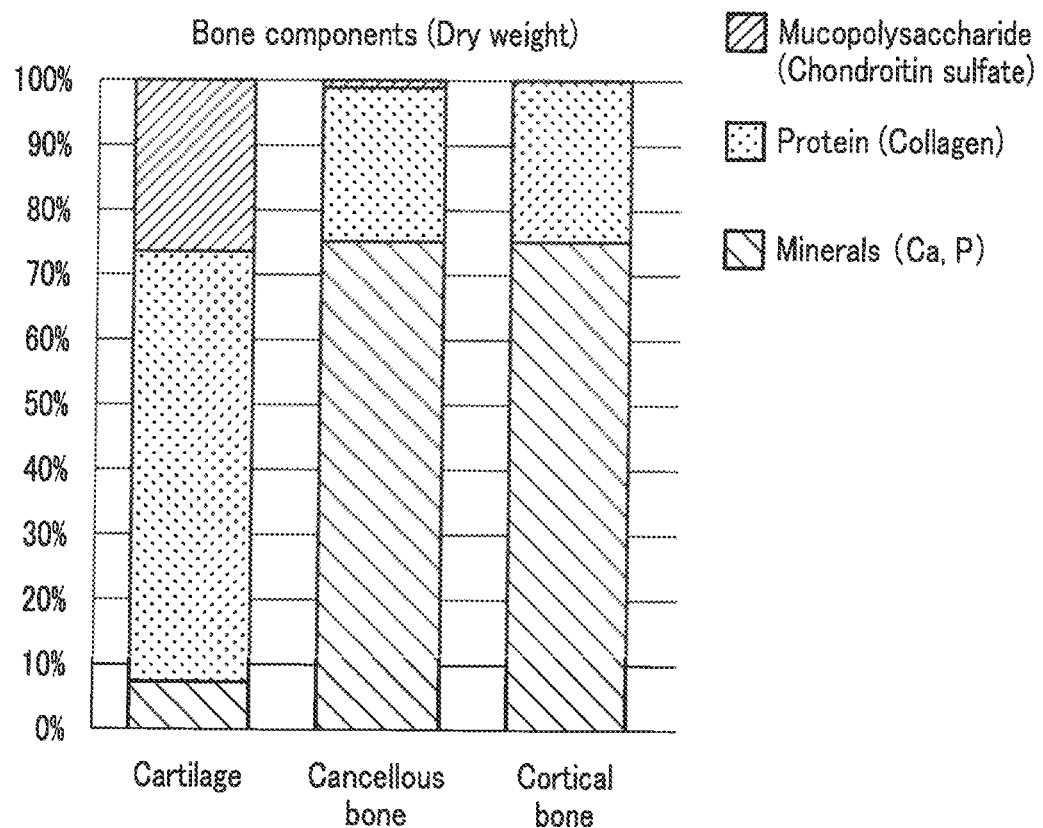
FIG. 1 illustrates components of cartilage, cancellous bone, and cortical bone.

FIG. 1 illustrates components of cartilage, cancellous bone, and cortical bone. As shown in FIG. 1, the main component of the cortical bone and cancellous bone is calcium phosphate, whereas the main component of cartilage is protein (collagen). Collagen is elastic and soft, unlike calcium phosphate. Accordingly, if an impulse is applied to collagen, the impulse is absorbed. Because of this characteristic, it is difficult to excise by applying an impulse cartilage whose main component is collagen.

Figure 2:
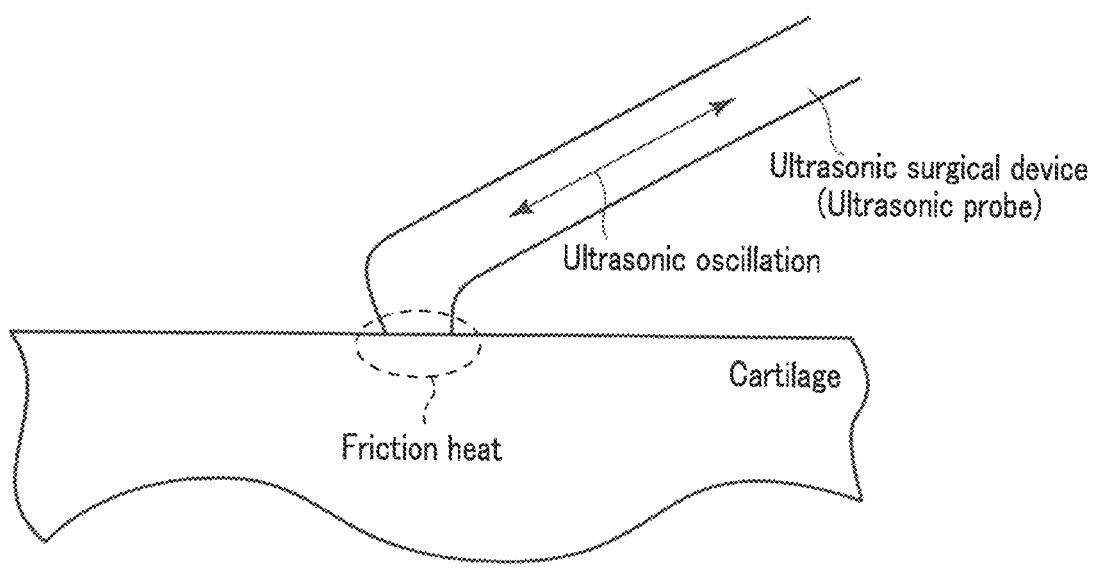
FIG. 2 illustrates the principle of cartilage excision by an ultrasonic surgical system.

However, the applicant found out that an ultrasonic surgical system can excise cartilage. As stated above, cartilage absorbs an impulse. The ultrasonic surgical system excises cartilage by bringing an ultrasonic excision device (ultrasonic probe) into contact with cartilage, causing the ultrasonic probe to ultrasonically vibrate in a direction indicated by an arrow of FIG. 2 to generate friction heat at a position where the ultrasonic probe is in contact with cartilage. By the generated friction heat, cartilage is melted and excised. FIG. 2 illustrates an example of an ultrasonic surgical system. However, the excision of cartilage by heating may also be performed by using a heating device, instead of the ultrasonic surgical system. The excision of cartilage by heating will be explained in more detail.

Figure 3A:
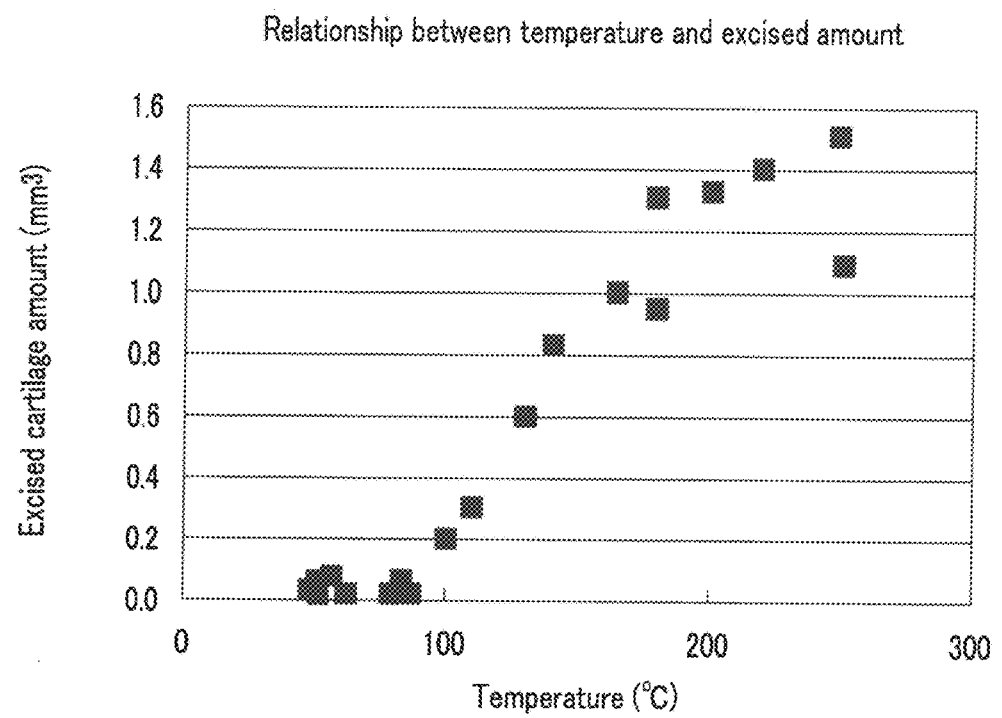
FIG. 3A illustrates the relationship between the amount of cartilage excision and the temperature when a soldering iron is pressed onto cartilage with a predetermined pressure.
Figure 3B:
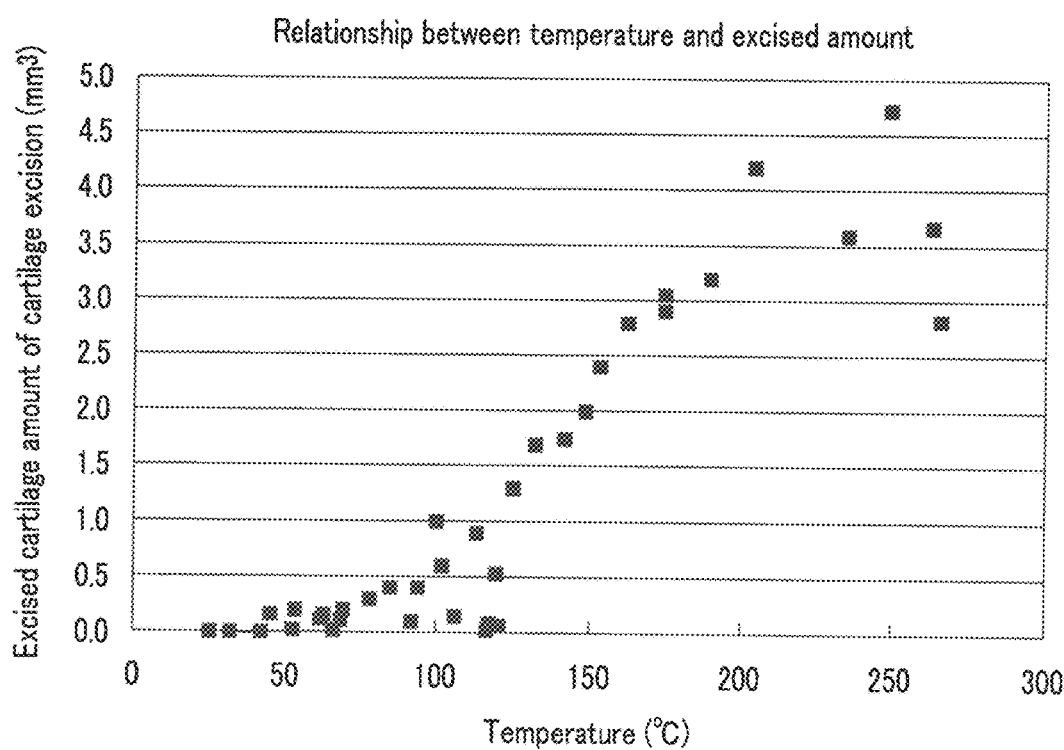
FIG. 3B illustrates the relationship between the amount of cartilage excision and the temperature when an ultrasonic excision device is pressed onto cartilage with a predetermined pressure.

FIGS. 3A and 3B illustrate the relationship between the temperature of cartilage and the amount of excision. FIG. 3A illustrates the relationship between the amount of cartilage excision and the temperature of cartilage when a soldering iron is pressed onto the cartilage with a predetermined pressure (2.94N). FIG. 3B illustrates the relationship between the amount of cartilage excision and the cartilage temperature when an ultrasonic excision device is pressed onto the cartilage with a predetermined pressure (2.94N). The horizontal axes of FIGS. 3A and 3B indicate the temperature (° C.) of the living tissue (cartilage). The vertical axes of FIGS. 3A and 3B indicate the amount of cartilage excision ($mm^3$). FIG. 4 illustrates the surface and the cross sectional view of cartilage for each of the temperatures when the soldering iron is pressed onto the cartilage. FIG. 4 illustrates the surface and the cross sectional view of cartilage at 40° C., 80° C., 120° C., 160° C., 200° C., and 240° C.

If the cartilage temperature is lower than 45° C., the cartilage is not excised as shown in FIGS. 3A and 3B. The surface and the cross sectional view of cartilage for temperatures lower than 45° C. are shown as those at 40° C. in FIG. 4.

If the temperature of cartilage is within the range of 45° C. to 120° C., the amount of cartilage excision becomes greater as the temperature becomes higher. The amount of excision does not greatly change according to the temperature within the range of 45° C. to 120° C. The surface and the cross sectional view of cartilage for temperatures within the range of 45° C. to 120° C. are shown as those at 80° C. in FIG. 4.

If the cartilage temperature is within the range of 120° C. to 160° C., the amount of cartilage excision becomes sharply greater as the temperature becomes higher. The surface and the cross sectional view of cartilage for temperatures within the range of 120° C. to 160° C. are shown as those at 120° C. in FIG. 4. The cartilage excision progresses significantly within this range.

If the cartilage temperature is within the range of 160° C. to 200° C., the amount of cartilage excision increases slightly as the temperature becomes higher. The surface and the cross sectional view of cartilage for temperatures within the range of 160° C. to 200° C. are shown as those at 160° C. in FIG. 4. If the cartilage temperature becomes 160° C., the cartilage excision progresses, but the surface of cartilage starts getting burned.

If the temperature of cartilage exceeds 200° C., the burn is expanded, and the amount of excision will be unstable, as shown in FIGS. 3A and 3B. The surface and the cross sectional view of cartilage for the temperature over 200° C. are shown as those at 200° C. and 240° C. in FIG. 4. If the cartilage temperature exceeds 200° C., the surface of the burnt cartilage will be expanded.

As shown in FIG. 3A, cartilage is excised even by applying heat with the soldering iron. Accordingly, it is understood that cartilage is excised if heat is applied to cartilage by any means except for the ultrasonic excision device. However, cartilage is not excised simply by applying heat if the temperature is lower than 45° C. Thus, it is necessary to heat the cartilage to a temperature of 45° C. or more to excise the cartilage. In addition, if the cartilage temperature exceeds 200° C., the cartilage is subjected to significant heat insult. Thus, it is desirable to heat the cartilage to a temperature of 220° C. or less to excise the cartilage. In consideration of a balance between the amount of cartilage excision and heat insult, it is desirable to heat the cartilage to a temperature of 120° C. to 160° C. to excise the cartilage.

Furthermore, as can be understood from the comparison between FIGS. 3A and 3B, the amount of cartilage excision for a certain temperature is greater when using the ultrasonic excision device than when using the soldering iron. The reason is because the ultrasonic excision device not only heats the cartilage, but also ablates the melted cartilage away by ultrasonic vibration. If the ultrasonic excision device is used for arthroscopic surgery performed in the state where a liquid fills joint cavities, the liquid is stirred by the ultrasonic vibration of the ultrasonic excision device. Since the part of the cartilage that has been melted is eliminated by this action, in addition to excision by the ultrasonic vibration, a large amount of cartilage can be excised for a certain temperature. That is, if the ultrasonic excision device is used for arthroscopic surgery, a larger amount of cartilage can be excised in a short time.

As stated above, when heat is used for excising cartilage, it is preferable to apply the heat only to a predetermined area to which the treatment is necessary. For example, if the cartilage to be excised is cartilage of a human body, there is a specific treatment target such as damaged cartilage or denatured cartilage. Accordingly, it is preferable that the temperature of only a treatment target such as damaged cartilage or denatured cartilage is increased, and the temperature of the peripheral healthy cartilage, subcartilaginous bone, and cancellous bones under the cartilage is not increased. In general, the cell structure of a human body such as cancellous bones or cortical bones may be damaged at about 40° C. For the aforementioned cartilage treatment, it is preferable to set the temperature of cartilage to be 120° C. to 160° C.

In consideration of the above, it is preferable that the temperature of the treatment target, such as damaged cartilage or denatured cartilage, is set as soon as possible to be approximately 120° C., and that the treatment is then completed before the temperature of healthy tissue around the treatment target that is not a treatment target, such as a cancellous bone, increases. In general, a cancellous bone may be damaged at around 40° C. Accordingly, it is preferable that the temperature of the cancellous bone has not been increased to 40° C. when the temperature of the cartilage or the denatured cartilage becomes 120° C.

Figure 5A:
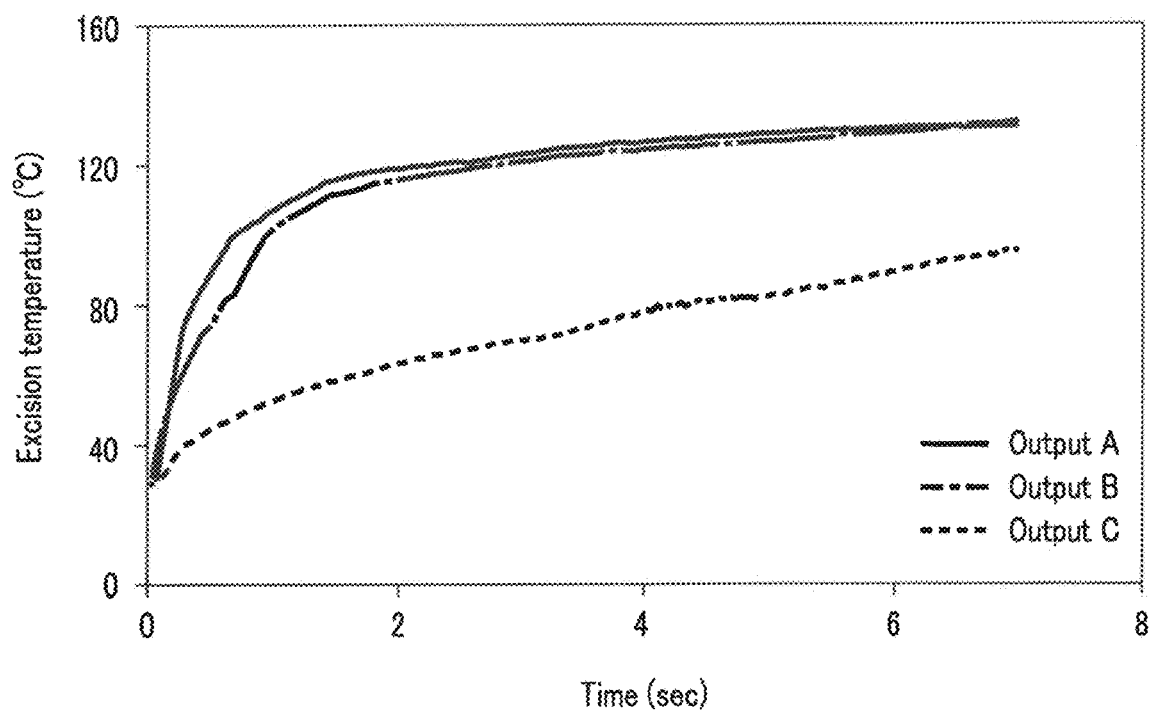
FIG. 5A illustrates an increase of the temperature of a cartilage over time when the ultrasonic excision device in which different outputs are applied is pressed onto cartilage.
Figure 5B:
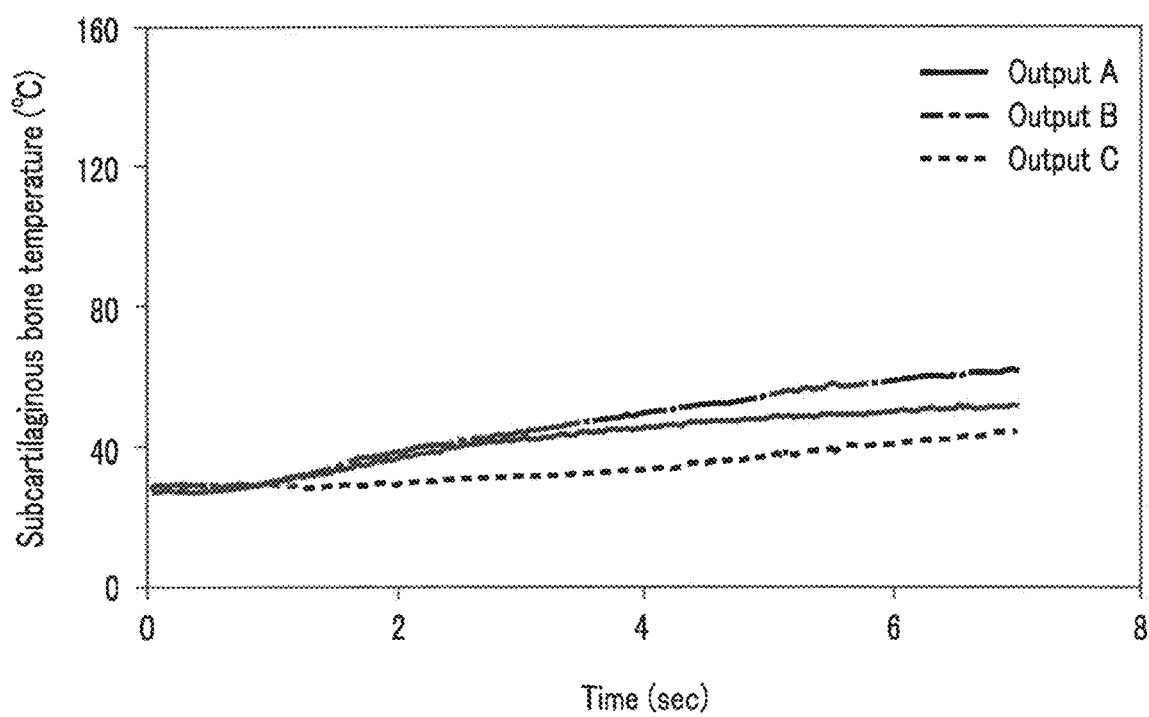
FIG. 5B illustrates an increase of the temperature of a subcartilaginous bone over time when the ultrasonic excision device is pressed onto cartilage with outputs A, B, and C of FIG. 5A.

FIG. 5A illustrates the increase of the temperature of a cartilage over time when the ultrasonic excision device in which different outputs are applied is pressed onto cartilage. The output A in FIG. 5A is an output adjusted so that the cartilage temperature becomes 120° C. in 2.2 seconds. The output B in FIG. 5A is an output adjusted so that the cartilage temperature becomes 120° C. in 2.8 seconds. The output C in FIG. 5A is an output adjusted so that the cartilage temperature becomes 120° C. in approximately 20 seconds. On the other hand, FIG. 5B illustrates the increase of the temperature of a subcartilaginous bone over time when the ultrasonic excision device is pressed onto cartilage with outputs A, B, and C of FIG. 5A. For the output A with which the temperature of cartilage becomes 120° C. in 2.2 seconds, the temperature of the subcartilaginous bone does not exceed 40° C. when the temperature of cartilage becomes 120° C. On the other hand, for the output B with which the temperature of cartilage becomes 120° C. in 2.8 seconds, the temperature of the subcartilaginous bone exceeds 40° C. before the temperature of cartilage becomes 120° C., as shown in FIG. 5B. Similarly, for the output C with which the temperature of cartilage becomes 120° C. in 20 seconds, the temperature of the subcartilaginous bone exceeds 40° C. before the temperature of cartilage becomes 120° C., as shown in FIG. 5B.

Figure 6A:
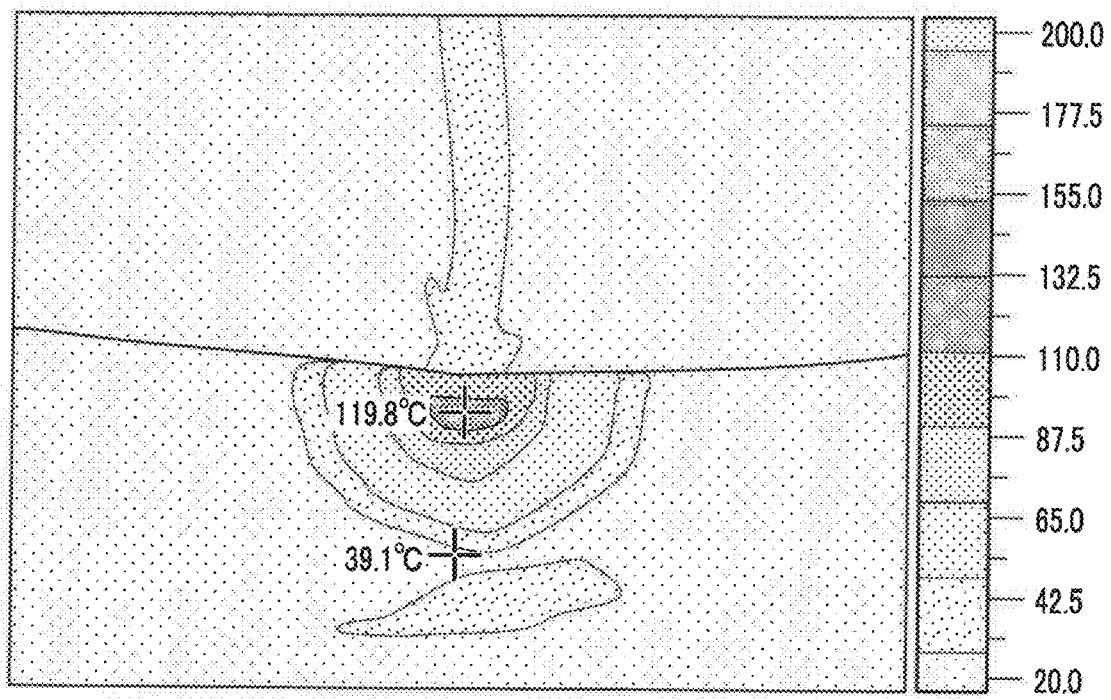
FIG. 6A is a schematic diagram of temperature distribution of cartilage, subcartilaginous bone, and cancellous bone when the temperature of the cartilage is 120° C. at output A.
Figure 6B:
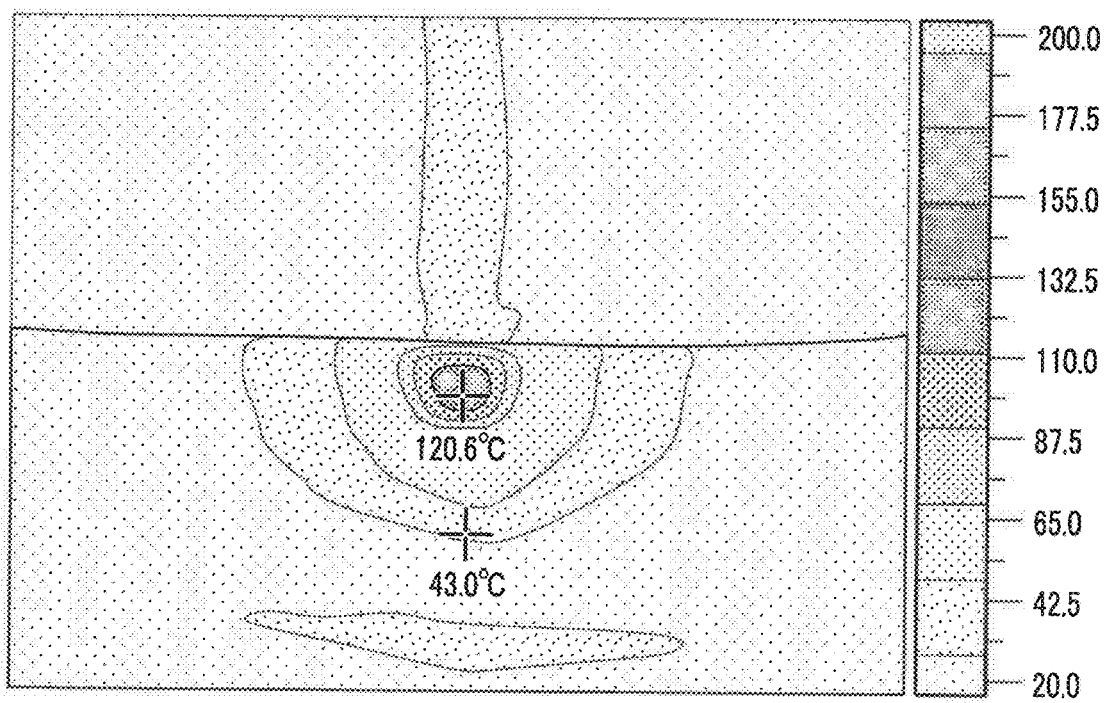
FIG. 6B is a schematic diagram of temperature distribution of cartilage, subcartilaginous bone, and cancellous bone when the temperature of the cartilage is 120° C. at output B.
Figure 6C:
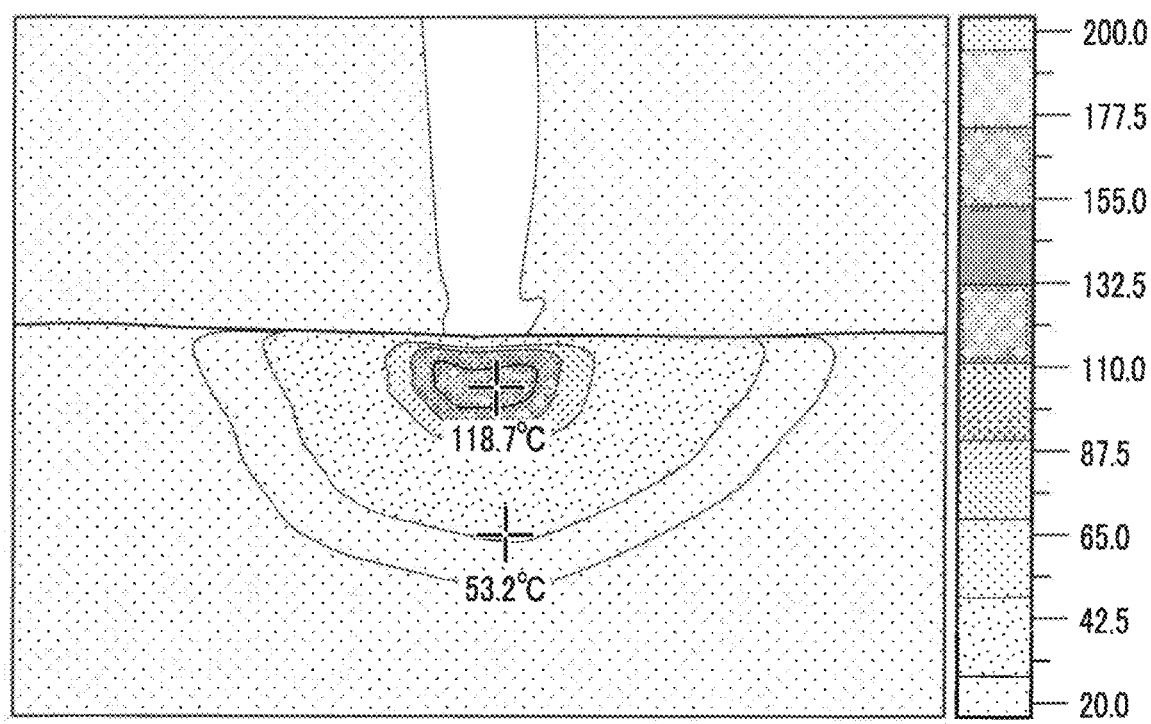
FIG. 6C is a schematic diagram of temperature distribution of cartilage, subcartilaginous bone, and cancellous bone when the temperature of the cartilage is 120° C. at output C.

FIG. 6A is a schematic diagram of a temperature distribution of cartilage and cancellous bone when the temperature of the cartilage is 120° C. at output A. As shown in FIG. 6A, when the operation is performed for 2.2 seconds, only the temperature of cartilage becomes high, and the increase of the temperature of subcartilaginous bone and cancellous bone around the cartilage can be suppressed. FIG. 6B is a schematic diagram of temperature distribution of cartilage, and cancellous bone when the temperature of the cartilage is 120° C. at output B. As shown in FIG. 6B, when the operation is performed for 2.8 seconds, heat transmitted to cartilage is transmitted to the subcartilaginous bone and the cancellous bone, and the temperature of the cancellous bone exceeds 40° C. FIG. 6C is a schematic diagram of a temperature distribution of cartilage and cancellous bone when the temperature of the cartilage is 120° C. at output C. In the example shown in FIG. 6C, the temperature of the subcartilaginous bone and the cancellous bone exceeds 40° C. before the temperature of cartilage sufficiently increases.

As can be seen from above, it is desirable that the operation of the ultrasonic excision device is performed within 2.2 seconds. That is, the surgical system suitable for treating human cartilage can be realized by adjusting the output, etc. so that the temperature of cartilage becomes 120° C. within 2.2 seconds.

First Embodiment

Figure 7:
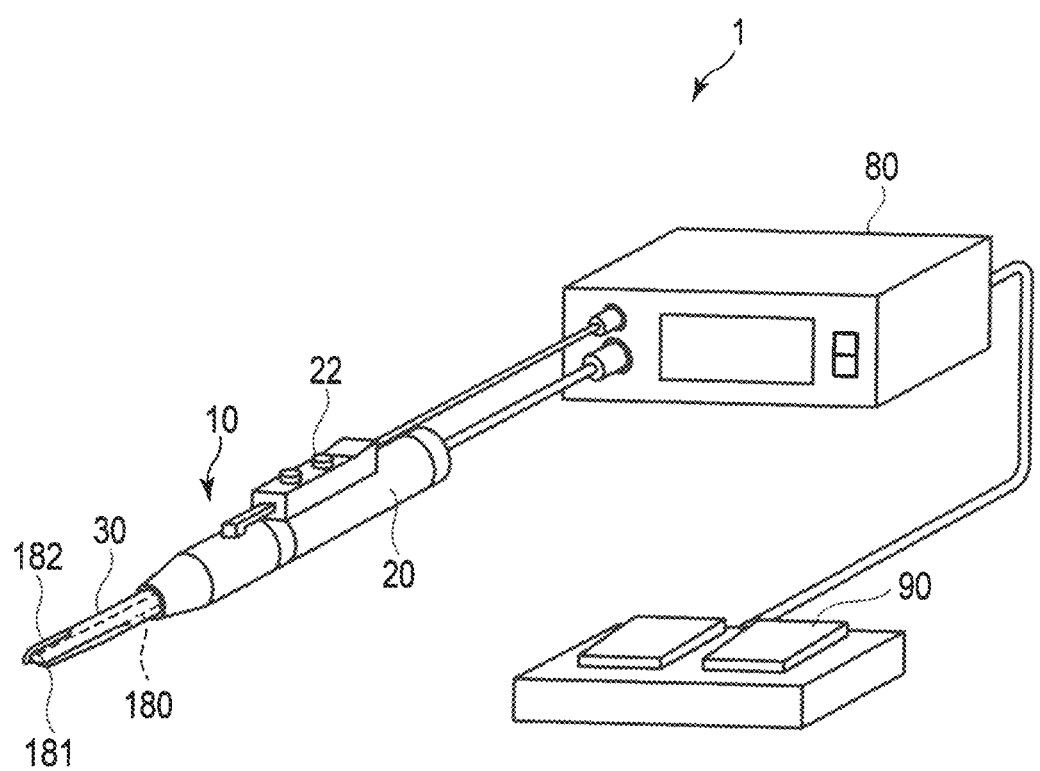
FIG. 7 illustrates an example of a detailed configuration of the surgical system according to the embodiments of the present invention.

The first embodiment is explained below. FIG. 7 illustrates an example of a detailed configuration of the surgical system according to the embodiments of the present invention. As stated above, excision of cartilage is performed by heating the cartilage to a suitable temperature. Any means for heating the cartilage to a suitable temperature can be used. For example, the surgical system of the present embodiment may adopt a system that heats cartilage to a temperature of 45° C. to 220° C., preferably, 120° C. to 160° C., by friction heat via ultrasonic vibration; a system that heats cartilage to a temperature of 45° C. to 220° C., preferably 120° C. to 160° C., by a heater; or a system that heats cartilage to a temperature of 45° C. to 220° C., preferably 120° C. to 160° C., by applying a radio frequency current. FIG. 7 illustrates an ultrasonic surgical system 1 as an example of the surgical system according to the present embodiment.

The ultrasonic surgical system 1 shown in FIG. 7 includes an excision device 10 that treats a living tissue by ultrasonic waves, a power supply device 80 that supplies driving power to the excision device 10, and a foot switch 90. The ultrasonic surgical system 1 is suitable for treating cartilage. However, the ultrasonic surgical system 1 may be used for treating a living tissue other than cartilage.

The excision device 10 functioning as an energy excision device includes a hand piece 20, a probe 180 protruding from the hand piece 20, and a slender-shaped sheath 30 formed around the probe 180. In the explanations below, the side of the excision device 10 where the probe 180 is provided is called a distal end, and the side of the excision device 10 where the hand piece 20 is provided is called a proximal end.

The hand piece 20 includes an ultrasonic transducer therein. The ultrasonic transducer ultrasonic vibrates in accordance with the driving power from the power supply device 80. The hand piece 20 transmits the ultrasonic vibration generated at the ultrasonic transducer to the probe 180. The probe 180 is connected to the ultrasonic transducer, and vibrates according to the vibration of the ultrasonic transducer.

The distal end of the sheath 30 has a semi-cylindrical shape, and the excision portion 181 provided at the distal end of the probe 180 is exposed from the semi-cylindrical portion. The distal end of the sheath 30 is provided with a cold knife 182, for example. The cold knife 182 is formed of a corrosion-resistant metallic material, and is used to facilitate excision of a living tissue. The cold knife 182 may be omitted.

The hand piece 20 includes an input unit 22. The input unit 22 is to input an instruction for driving the ultrasonic transducer. The input unit 22 may include a plurality of switches so that the driving of a plurality of types of ultrasonic transducers may be carried out according to a plurality of types of inputs. The plurality of switches includes a switch to drive the ultrasonic transducer suitable for treatment of the cartilage. The input unit 22 is connected to the power supply device 80. The ultrasonic transducer within the hand piece 20 is connected to the power supply device 80. The power supply device 80 detects an input to the input unit 22, and supplies driving power to the ultrasonic transducer in accordance with the detected input.

The foot switch 90 has a function similar to that of the input unit 22 provided to the hand piece 20. That is, the foot switch 90 includes a switch similar to the input unit 22. The foot switch 90 may include a plurality of switches, similar to the input unit 22. If the power supply device 80 detects an input to the foot switch 90, the power supply device 80 supplies a driving electric power to the ultrasonic transducer in accordance with the detected input. At least one of the input unit 22 and foot switch 90 may be provided.

When performing treatment, a user holds the hand piece 20 and brings the excision portion 181 provided in the probe 180 that is ultrasonically vibrating into contact with a living tissue that is a treatment object. The user operates the input unit 22 or the foot switch 90 to vibrate the ultrasonic transducer at this time. The vibration generated at the ultrasonic transducer is transmitted to the probe 180. The living tissue is cut or excised by bringing the excision portion 181 of the probe 180 that is vibrating into contact with the living tissue.

FIG. 8 is a block diagram illustrating the main configuration of the ultrasonic surgical system 1 according to the first embodiment of the present invention. In FIG. 8, the same structures as explained with reference to FIG. 7 are indicated with the same reference numerals, and the explanations thereof will be omitted.

As shown in FIG. 8, the power supply device 80 includes an output circuit 81 and a control circuit 82.

The output circuit 81 is electrically connected to an ultrasonic transducer 24, and generates driving power to drive the ultrasonic transducer 24 provided inside of the hand piece 20 of the excision device 10. Based on the driving power, an output voltage and an output current are output from the output circuit 81 to the excision device 10.

Figure 9:
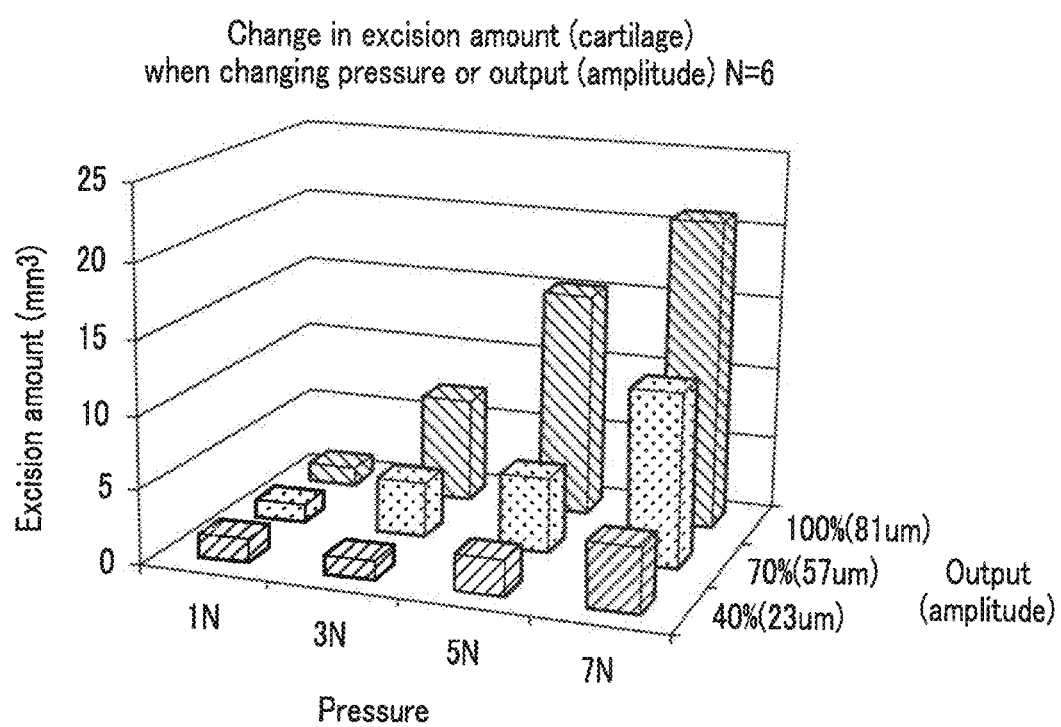
FIG. 9 is a graph showing the experimental results of measuring the change in the amount of excision when a pressure or an amplitude relative to cartilage is changed.

The control circuit 82 is configured by an ASIC including a CPU, for example, and controls the driving power of the output circuit 81 in accordance with an input from the input unit 22 or the foot switch 90. For example, if an instruction to enter the cartilage excision mode is made by the input from the input unit 22 or the foot switch 90, the control circuit 82 controls the output circuit 81 to allow the ultrasonic vibration to be generated at the excision device 10 to increase the temperature of cartilage to the aforementioned temperature, namely 45° C. to 220° C., preferably to 120° C. to 160° C. For the ultrasonic surgical system, the cartilage temperature changes in accordance with the friction heat. Based on the applicant's analysis, it is understood that the heating amount by friction heat is determined based on the amplitude of the ultrasonic vibration and the pressure when pressing the excision device 10 to the cartilage, as shown FIG. 9. Thus, if the pressure is fixed the average value of the pressure when a doctor presses the excision device 10 onto a living tissue, the friction heat only changes by the amplitude. In the present embodiment, amplitude where cartilage is heated to 45° C. to 220° C., preferably to 120° C. to 160° C., is measured in experiments with the fixed pressure, and the measured amplitude values are stored in a memory 821 of the control circuit 82. The control circuit 82 reads the amplitude value from the memory 821, and controls the output current and the output voltage of the output circuit 81 so that the ultrasonic transducer 24 vibrates with the read amplitude value.

In addition, as stated above, it is preferable that the temperature of the treatment target is increased to 120° C. in approximately 2.2 seconds. If the amplitude of ultrasonic vibration is simply increased, it is possible to increase the temperature of the treatment target for a short time in the ultrasonic surgical system. Furthermore, it is possible to increase the temperature of the treatment target in a shorter time by increasing the pressure applied to the excision portion.

Figure 10:
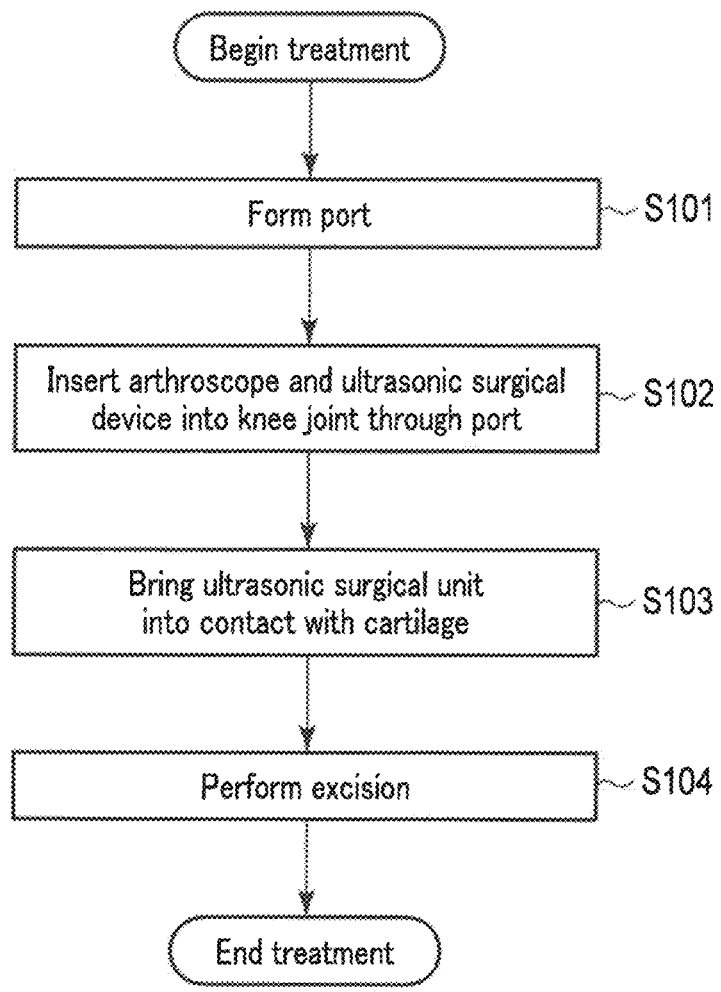
FIG. 10 is a flowchart illustrating the treatment using the ultrasonic surgical system.

The operation of the ultrasonic surgical system 1 of the present embodiment will be explained below. FIG. 10 is a flowchart illustrating the treatment using the ultrasonic surgical system 1 in the first embodiment. The treatment shown in FIG. 10 is the excision of degenerated cartilage at a knee joint. The treatment flow shown in FIG. 10 is not limited to a knee joint, but may be applied to other joints such as a shoulder joint.

In step S101, a doctor uses a trocar to form a port through which an excision device and an arthroscope can be inserted into a position of a living tissue to be treated (in this case, degenerated cartilage at a knee joint).

In step S102, the doctor inserts the arthroscope and the excision device 10 of the ultrasonic surgical system 1 into the knee joint through the port for the arthroscope.

In step S103, the doctor brings the excision portion 181 of the ultrasonic surgical system 1 into contact with the degenerated cartilage to be treated while watching an image of the knee joint displayed on a monitor through the arthroscope.

In step S104, the doctor, for example, operates the input unit 22 sets the ultrasonic surgical system 1 to the cartilage mode, and starts excision of the degenerated cartilage. If the ultrasonic surgical system 1 is set to the cartilage mode, the control circuit 82 reads the amplitude value pre-stored in the memory 821 (for example, the amplitude value required to heat the cartilage to 120° C.), and controls the output circuit 81 so that the ultrasonic transducer 24 vibrates at the read amplitude. By bringing the excision portion 181 vibrating at the read amplitude into contact with the denatured cartilage with a fixed pressure, the temperature of the degenerated cartilage becomes about 120° C. The degenerated cartilage is then melted, and excised. The value of amplitude in step S104 is preferably a value required to increase the temperature of cartilage to 120° C. in a predetermined short time (within 2.2 seconds). By this process, the treatment is completed in a short time, and an unnecessary increase in the temperature of a non-treatment target is prevented.

In accordance with the aforementioned embodiment, the amount of cartilage heating by the excision device 10 is controlled to heat the cartilage to a temperature of 45° C., by paying attention to the fact that the cartilage heated to 45° C. or higher is melted and excised. By this procedure, cartilage can be reliably excised.

In addition, according to the present embodiment, the heating amount of the cartilage by the excision device 10 is controlled to heat the cartilage to be within the predetermined range of 45° C. to 220° C., preferably within 120° C. to 160° C., in consideration of heat insult to the cartilage. By this procedure, cartilage can be excised with a small amount of heat insult.

Furthermore, according to the present embodiment, the treatment can be completed in a short time by treating cartilage by the excision portion 10. Accordingly, an unnecessary increase in the temperature of a non-treatment target that does not need treatment is prevented.

In the aforementioned embodiment, the ultrasonic surgical system is illustrated as a surgical system. In the present embodiment, it is possible to apply a surgical system using a heater, a surgical system using a radio frequency current, or a combination thereof using energy different from ultrasonic waves, other than the ultrasonic surgical system if the cartilage can be heated to the predetermined range of 45° C. to 220° C., preferably to 120° C. to 160° C. However, the ultrasonic surgical system can reduce the amount of heat insult in comparison with the surgical system using a heater or a radio frequency. In addition, the ultrasonic surgical system can excise the cartilage to make the excised surface smooth in comparison with the surgical system using a heater or radio frequency. Furthermore, the ultrasonic surgical system can excise a larger amount of cartilage in comparison with the surgical system using a motor.

FIG. 11 illustrates the comparison of cartilage excision results between a radio-frequency surgical system (RF) and an ultrasonic surgical system (US). FIG. 11 also includes the cartilage excision results of a surgical system using a drill (BUR) (i.e., results of impulse-only excision) for comparison. As shown in FIG. 11, the cartilage is hardly excised by the impulse-only excision treatment. Rather, the cartilage surface becomes villus-like shaped, without retaining its original shape. On the other hand, with the excision treatment using radio frequency, the amount of excision is larger than the treatment using a drill; however, the amount of heat insult is relatively extensive. In comparison with the above, with the excision treatment using ultrasonic waves, greater progress is made in cartilage excision, while relatively suppressing the amount of heat insult.

Figure 12:
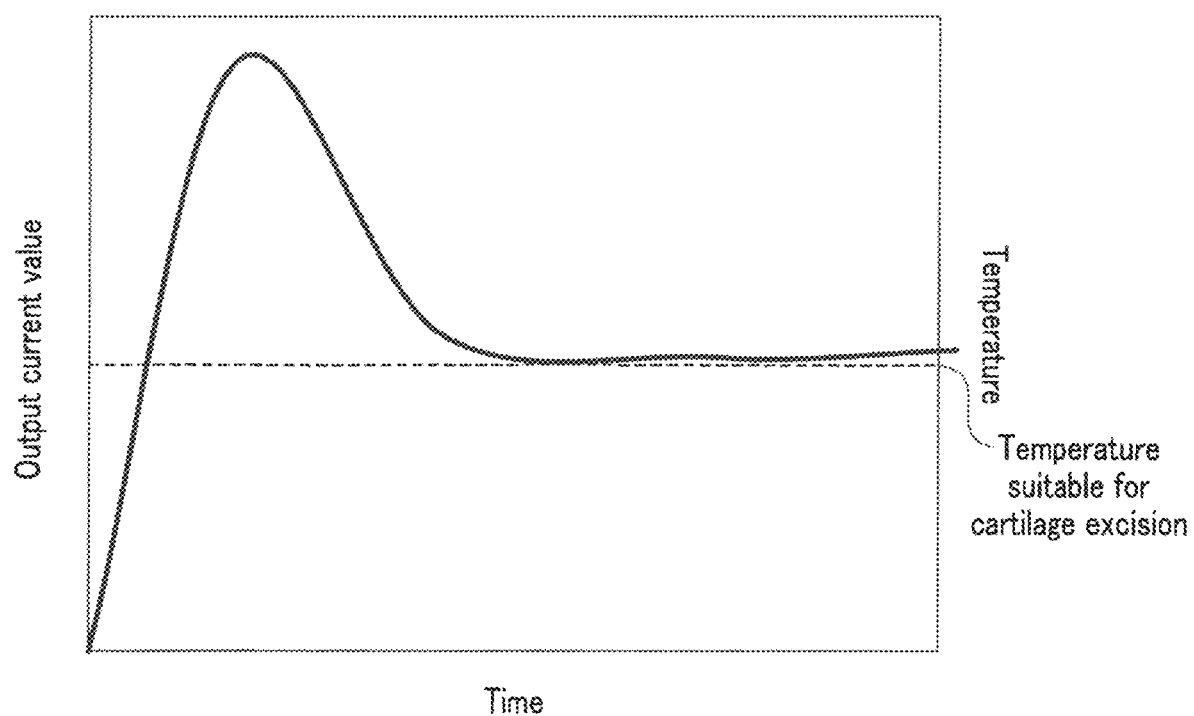
FIG. 12 illustrates a variation example in which an output current is overshot.

It is known that the speed of an increase in heat is slower when using the ultrasonic surgical system than when using the radio-frequency surgical system. Thus, it is possible to overshoot the output current in comparison with the output current corresponding to the desired amplitude only during a predetermined period of time immediately after starting the ultrasonic surgical system, as shown in FIG. 12, so that the temperature of the cartilage reaches the target temperature faster.

Second Embodiment

The variation example of the embodiment will be explained below. In the aforementioned embodiment, the amount of cartilage heating by the excision device 10, to heat the cartilage to the temperature suitable for excision, is controlled in accordance with a setting (for example, amplitude) predetermined by actual measurements. In the second embodiment, the amount of cartilage heating by the excision device 10 is feedback controlled.

Figure 13:
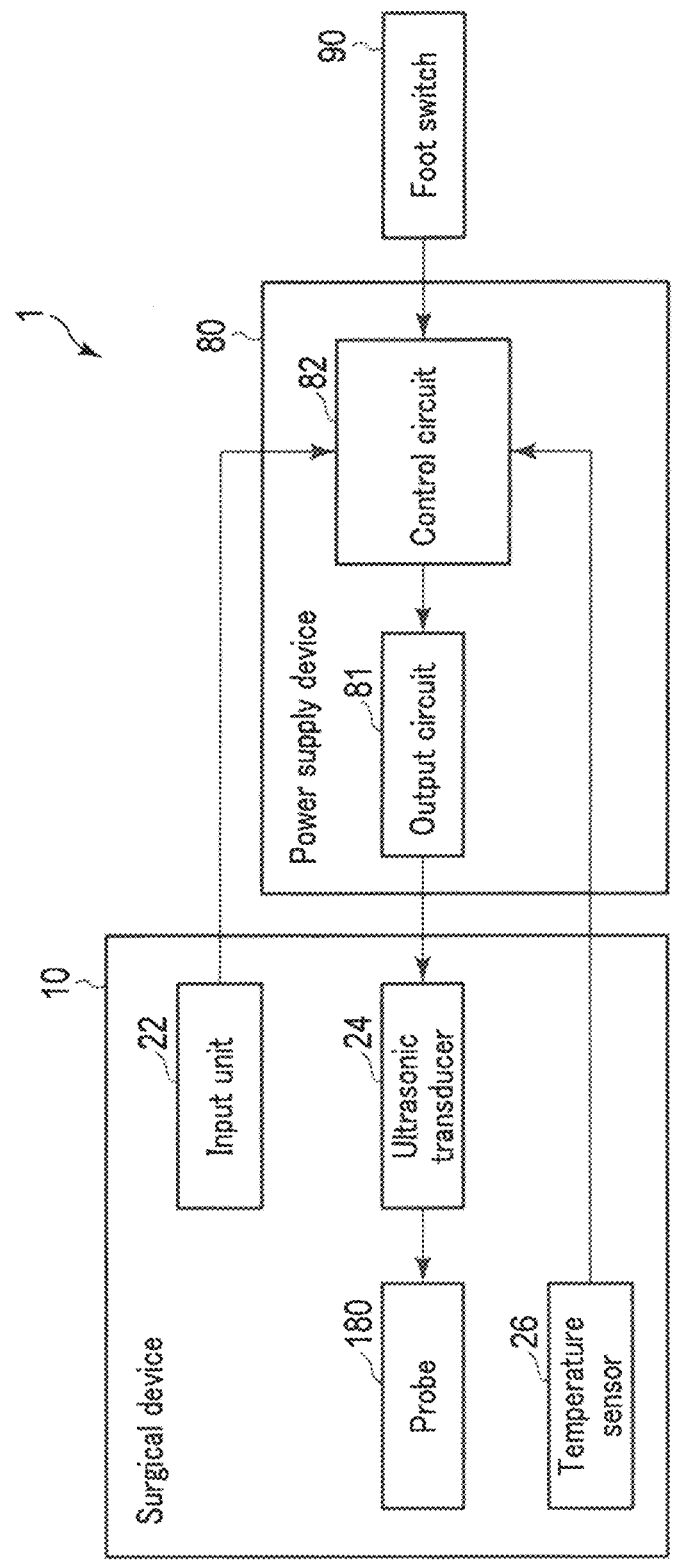
FIG. 13 is a block diagram showing a main configuration of the ultrasonic surgical system according to the second embodiment of the present invention.

FIG. 13 is a block diagram illustrating the main configuration of the ultrasonic surgical system 1 according to the second embodiment of the present invention. In FIG. 13, the same structures as explained with reference to FIG. 8 are indicated with the same reference numerals, and the explanations thereof will be omitted.

The excision device 10 of the ultrasonic surgical system 1 according to the second embodiment includes a temperature sensor 26. The temperature sensor 26 is provided within the distal end of the excision device 10, for example, detects the temperature of the distal end of the excision device 10, i.e., the temperature of cartilage, and inputs a signal according to the detected temperature to the control circuit 82 of the power supply device 80. Various temperature sensors such as a thermocouple and a thermistor may be used as the temperature sensor 26.

The control circuit 82 according to the second embodiment controls the output circuit 81 to maintain the temperature measured by the temperature sensor 26 at a predetermined temperature within the range of 45° C. to 220° C., preferably within 120° C. to 160° C. For example, the control circuit 82 controls the output circuit 81 to increase the output current from the output circuit 81 if the temperature measured by the temperature sensor 26 is below the predetermined temperature. In addition, the control circuit 82 controls the output circuit 81 to decrease the output current from the output circuit 81 if the temperature measured by the temperature sensor 26 exceeds the predetermined temperature.

According to the aforementioned second embodiment, cartilage is more reliably excised by performing feedback control to the output power from the output circuit 81 in accordance with the cartilage temperature measured by the temperature sensor, in comparison with the first embodiment. In the second embodiment, it is possible to omit the memory 821 applied in the first embodiment.

In the second embodiment, the temperature of the cartilage is measured by the temperature sensor 26. However, the cartilage temperature is not limited to being measured by the temperature sensor.

Third Embodiment

The third embodiment is explained below. The third embodiment is a variation example of the treatment method. As described above, it is preferable that the temperature of only the treatment target is increased to 120° C. to 160° C. during the treatment, and the temperature of non-treatment target is below 40° C. With this purpose, the amplitude may be increased, or the pressure may be increased in the ultrasonic surgical system 1. The present embodiment accomplishes a shorter treatment by a particular treatment method.

Figure 14:
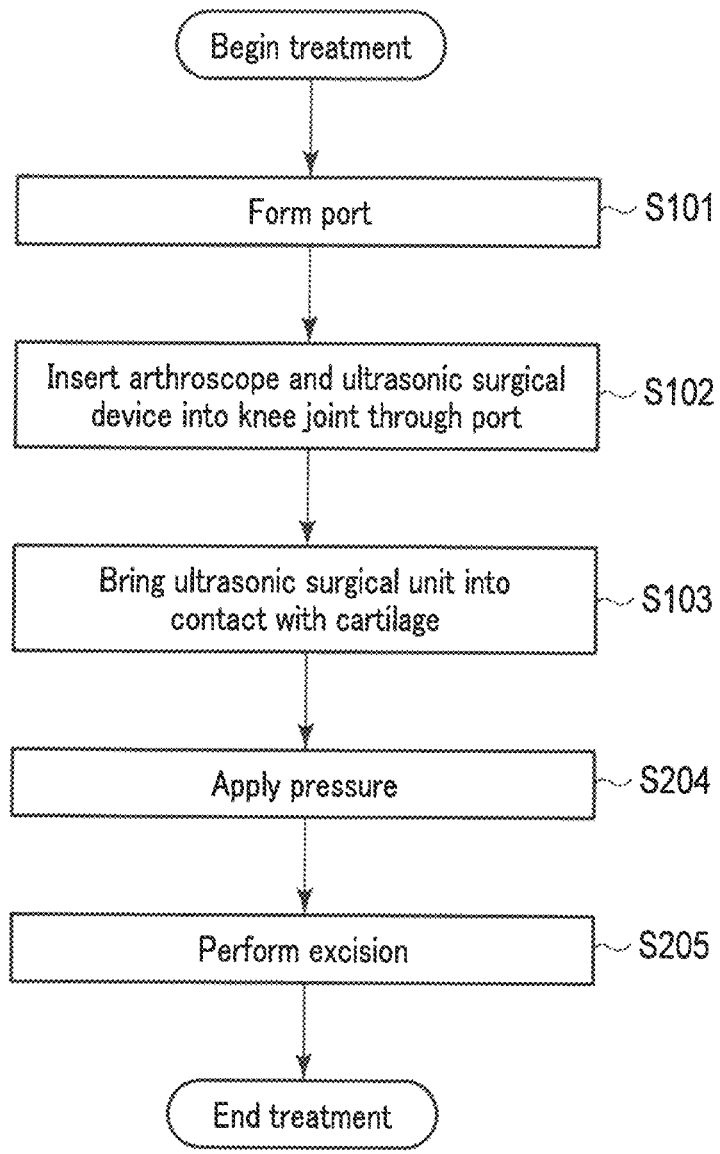
FIG. 14 is a flowchart illustrating the treatment using the ultrasonic surgical system in the third embodiment of the present invention.

FIG. 14 is a flowchart illustrating the treatment using the ultrasonic surgical system in the third embodiment. Similar to FIG. 10, the treatment shown in FIG. 14 is the excision of denatured cartilage at a knee joint. The treatment flow shown in FIG. 14 is not limited to a knee joint, but may be applied to other joints such as a shoulder joint. In FIG. 14, the explanations of the same structures as explained with reference to FIG. 10 will be omitted. That is, the processes at steps S101 to S103 will be omitted.

In step S204, the doctor, for example, operates the input unit 22 to set the ultrasonic surgical system 1 to the cartilage mode, and starts excision of the denatured cartilage. If the ultrasonic surgical system 1 is set to the cartilage mode, the control circuit 82 reads the amplitude value pre-stored in the memory 821 (for example, the amplitude value required to heat the cartilage to 120° C. within 2.2 seconds), and controls the output circuit 81 so that the ultrasonic transducer 24 vibrates at the read amplitude. By bringing the excision unit 181 vibrating at the read amplitude into contact with the denatured cartilage with a fixed pressure, the temperature of the denatured cartilage increases.

Figure 15:
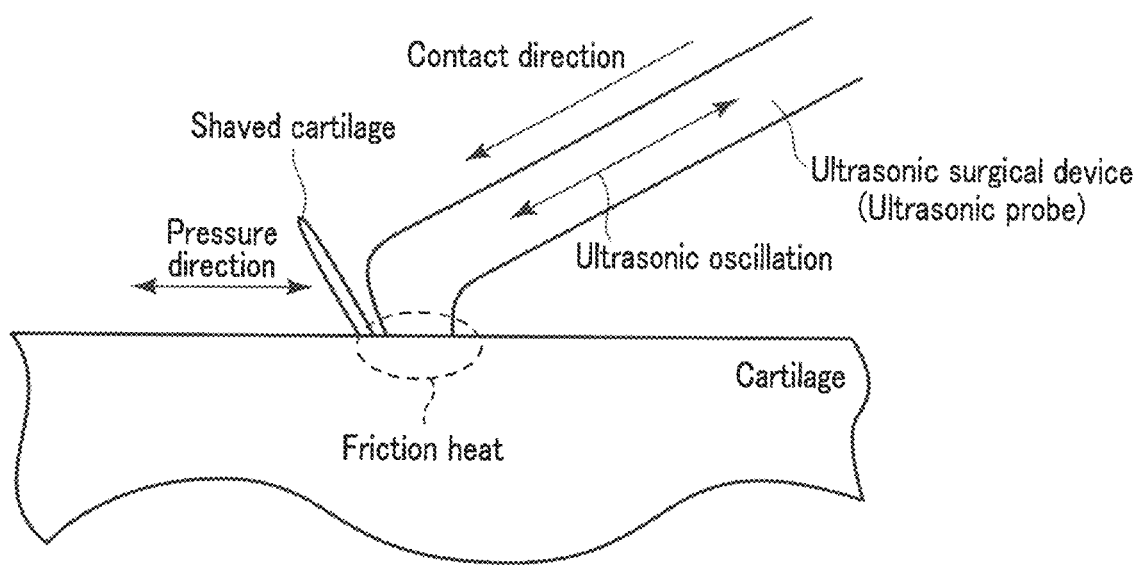
FIG. 15 is a diagram to explain the pressure of the excision portion in step S105.

In step S205, the doctor excises (energy-assisted trims, removes, or accurately shaves) cartilage by the probe 180, as shown in FIG. 15. The process shown in FIG. 15 indicates excising (paring) cartilage by generating a continuous amount of film-shaped shavings as in peeling away skin. Specifically, the doctor presses the excision unit 181 in the direction substantially parallel to the surface of cartilage, which is different from the direction of contact. By this process, a compressive force is applied to the cartilage, and the temperature of the cartilage increases further. The denatured cartilage is then melted and excised. In addition, by applying pressure to the excision unit 181 in the direction substantially parallel to the surface of the heated cartilage, the surface of the cartilage is shaved as a film, as shown in FIG. 15. Accordingly, the denatured cartilage is excised more efficiently.

According to the aforementioned embodiment, a more efficient excision of the denatured cartilage is realized by applying the pressure to the excision unit 181 in the direction substantially parallel to the surface of heated cartilage, in addition to the advantageous effects explained in the first embodiment. In step S205, the direction of pressing is different from the direction of contact. However, it may be possible to excise in the thickness (depth) direction of cartilage by pressing in the direction of contact.

The process at step S205 of the third embodiment can be applied to a surgical system using a heater, a surgical system using a high frequency current, or a combination thereof using energy different from ultrasonic waves, other than the ultrasonic surgical system.

The embodiments have been described, but the present invention is in no way limited to these embodiments. The present invention can, of course, be modified in various ways without departing from the spirit and scope of the invention.

What is claimed is:

1. A power supply device connected to an excision device configured to press a predetermined portion of a cartilage, melt the predetermined portion of the cartilage by friction heat generated by ultrasonic vibration generated by a transducer, and excise the predetermined portion of the cartilage, while being in contact with the predetermined portion of the cartilage, the device comprising:
   an output unit configured to generate a driving power to drive the transducer; and
   a controller configured to control the output unit to output the driving power to heat the predetermined portion of the cartilage to a temperature of 120° C. or higher within 2.2 seconds, and to maintain a temperature of the predetermined portion of the cartilage to be at 120° C. or higher.

2. The power supply device according to claim 1, further comprising:
   a memory configured to store a value of amplitude of the ultrasonic vibration required to heat the predetermined portion of the cartilage to the temperature of 120° C. or higher,
   wherein the controller controls the driving power output from the output unit in accordance with the value of amplitude stored in the memory.

3. The power supply device according to claim 1, wherein the controller controls the driving power to prevent a temperature of a subcartilaginous bone and a cancellous bone other than the predetermined portion of the cartilage from exceeding 40° C.

4. The power supply device according to claim 1, wherein the controller controls the driving power output from the output unit so that a temperature of the cartilage is prevented from exceeding 220° C.

5. The power supply device according to claim 1, wherein the controller controls the driving power output from the output unit so that a temperature of the cartilage is prevented from exceeding 160° C.

6. The power supply device according to claim 1, wherein the controller controls the driving power output from the output unit so that the predetermined portion of the cartilage is heated to a temperature of 120° C. or more but 160° C. or less within 2.2 seconds, and a temperature of the predetermined portion of the cartilage is maintained to be at 120° C. or more but 160° C. or less.

* * * * *